United States Patent [19]

Jessel, Jr.

[11] Patent Number: Plant 7,483

[45] Date of Patent: Mar. 26, 1991

[54] CARNATION PLANT NAMED CFPC SABRE

[75] Inventor: Walter H. Jessel, Jr., Salinas, Calif.

[73] Assignee: California Florida Plant Company L.P., Salinas, Calif.

[21] Appl. No.: 478,529

[22] Filed: Feb. 9, 1990

[51] Int. Cl.[5] ..... A01H 5/00

[52] U.S. Cl. ..... Plt./73

[58] Field of Search ..... Plt./70–73

*Primary Examiner*—James R. Feyrer

*Attorney, Agent, or Firm*—James R. Cypher

[57] ABSTRACT

The present invention relates to a new and distinct cultivar of Carnation Plant named CFPC SABRE, a cross from breeding unnamed and unpatented seedlings identified as No. 00117 and No. RI 005, distinguished from its parents, as well as any other variety known to me, by its bright red color, abundant and stable production, fast growing response which does not slow down during cool periods, non-silvering under cool conditions, and when compared to the commercial variety of closest color, Rony, it has a three to four day longer vase-life, has less serrated petal edges and a higher crowned fuller appearance, and the petals are arranged so that anthers are less conspicious.

1 Drawing Sheet

BACKGROUND OF THE INVENTION

The present invention relates to a new and distinct cultivar of Carnation Plant named CFPC SABRE which was originated by me by crossing unnamed and unpatented seedlings in a controlled breeding program at commercial nurseries at Fremont and Salinas, Calif. The female, or seed parent was identified as No. 00117, and the male, or pollen parent, was identified as No. RI 005.

The primary objectives of this breeding were to produce a miniature red carnation cultivar of excellent color; abundant production with a fast growing response which would not slow down during cool periods or show color silvering; and a smoother, less serrated petal-edge.

These objectives were fully achieved, along with other desirable improvements, as evidenced by the following unique combination of principal characteristics which are outstanding in my new cultivar, CFPC SABRE, and which distinguish it from its parents, as well as from all other carnations of which I am aware. The closest commercial cultivar in color to the new cultivar is the commercially available, unpatented Carnation Plant named Rony.

The distinguishing characteristics which are outstanding in the new cultivar are as follows:

1. large, spray-type flowers which open fully without bursting the clayx and causing "splits";
2. a distinctive bright red flower color;
3. a very vigorous and free-breaking plant habit with strong, straight sprays;
4. pinched plants are shorter than pinched plants of Rony;
5. the foliage is very durable; not sensitive to firing;
6. flowring time is six weeks earlier than Rony;
7. color is lighter and brighter than Rony, and does not turn darker and blacker in cool temperatures as Rony does;
8. petal edges are less serrated than Rony, and flowers have a more formal, fuller appearance;
9. vase-life is 3 to 4 days longer than Rony's under equal conditions.

Asexual reproduction and flowerings of the new cultivar where performed by Applicant using side shoot cuttings rooted in peat and "Perlite" under mist, in commercial greenhouses with coverings of either glass, fiberglass or polyethylene plastic located at Fremont and Salinas, Calif. The new cultivar was found to retain its distinctive characteristics as listed herein through successive propagations.

BRIEF DESCRIPTION OF THE DRAWING

The accompanying color photograph illustrates typical specimens of the new carnation in different stages of development (tight buds, partially opened buds and flowers in full bloom) and shows the bright, red color and vigorous, free-breaking growth habit and strong, straight stems of CFPC SABRE. The color photograph depictes the color as nearly true as it is reasonably possible to do in a color illustration of this character.

DETAILED DESCRIPTION OF THE DRAWING

The following is a detailed description of the new carnation plant of the present invention based on observations of plants grown inside commercial greenhouses at Fremont and Salinas, Calif.; the height of plant, and flower and foliage size established as an average using standard commercial cultural practices. The data provided accurately characterizes the new cultivar in question. The color terminology used in the following is in accordance with The Royal Horticultural Society Colour Chart. Color designation and other values stated may deviate slightly from the stated values from flowering to flowering, but the deviations will be within the range expected from varying environmental, seasonal and cultural conditions.

PLANT

Name: CFPC SABRE.

Classification:

*Botanical.*—*Dianthus caryophyllus.*

*Commercial.*—Carnation, greenhouse type, suitable for cut flower production as a spray.

Origin:

*Female parent.*—unnamed and unpatented Carnation Plant identified as No. 00117.

*Male parent.*—Unnamed and unpatented Carnation Plant identified as No. RI 005.

The following table compares the new cultivar with its closest commercial variety of which I am aware.

TABLE OF COMPARISON

| New Cultivar CFPC SABRE | RONY |
|---|---|
| PLANT: | |
| Height 38" | 42" |
| Form: rounded, high crown | same |
| Growing Habit: stiff, semi-upright | same |
| Blooming Habit: spray, 6 to 7 buds and flowers | spray, 5 to 6 buds and flowers |
| Blooming Season: year-round | same |
| Rooting Time/Habit: 18 to 20 days | same |
| Stem: | |
| Color: green | same |
| Breaking action: excellent | same |
| Mutation Prone No | same |
| Temperature Tolerance: very good | good but will blacken if too cold |
| FOLIAGE: | |
| Color | |
| Upper side: grey-green 139B | same |
| Lower side: grey-green 138B | same |
| Size: | |
| 2" to 4¼" long | 2½" to 4½" long |
| ¼" to ⅜" wide | same |
| Quanty: numerous | same |
| Shape: lanceolate pointed elongated | same |
| Texture: smooth | same |
| Ribs: indented mid-rib | same |
| Arrangement: bi-laterial at nodes | same |
| BLOOM: | |
| Form: spray | same |
| Shape: rounded high crown | same |
| Inflorescence: 6 to 7 per stem | 5 to 6 per stem |
| flower: | |

-continued

TABLE OF COMPARISON

| New Cultivar CFPC SABRE | RONY |
|---|---|
| diameter average: 2¾" to 3" | 2¾" to 3¼" |
| depth: 1¼" | same |
| Borne: on elongated peduncles as a spray | same |
| Color: | |
| general tonality: red | dark red |
| Upper side: red group 46A–47A | red group 46A–45C |
| Lower side: red group 44A–44B | 46C |
| Center: 46A–47A | 46A–45C |
| Outer petals: 46A–47A | 46A–45C |
| Permanence yes | same |
| Keeping habit: 10 to 12 days | 8 to 10 days |
| Fragrance: slight | same |
| PETALAGE: | |
| Number: 28 to 29 | 27 to 28 |
| Outer petals, | |
| length 1¼" | 1½" |
| width ⅞" | 1" |
| Central petals, | |
| length ⅝" | ⅔" |
| width ⅜" | ½" |
| Texture: smooth | same |
| Appearance: smooth | same |
| Form: fan-shaped | same |
| REPRODUCTION ORGANS: | |
| Stamen: | |
| number: 8 to 9 | same |
| arrangement: whorled around base of ovary | same |
| anthers: color: white | same |
| Pistil: | |
| number: 2 | same |
| stigma: 2 | same |
| Pollen: | |
| color: white | same |
| abundant: yes | same |
| Fertility: average | same |

I claim:

1. A new and distinctive cultivar of Carnation Plant, named CFPC SABRE substantially as herein shown and described.

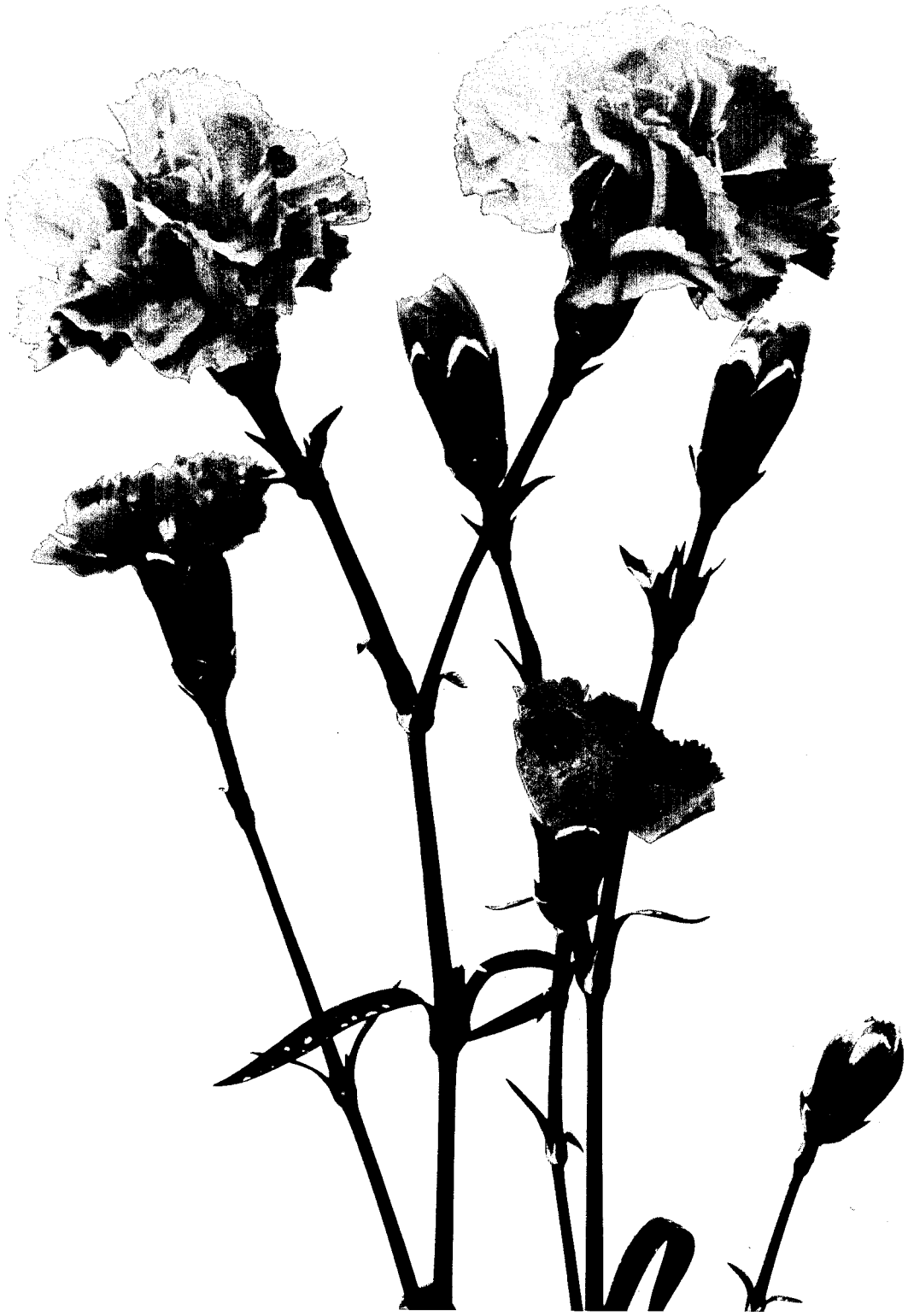

* * * * *